US012605059B2

(12) United States Patent
Fouts et al.

(10) Patent No.: US 12,605,059 B2
(45) Date of Patent: Apr. 21, 2026

(54) DYNAMICALLY RETRACTABLE CAMERA FOR VIDEO LARYNGOSCOPE

(71) Applicant: Verathon Inc., Bothell, WA (US)

(72) Inventors: Jason Fouts, Bothell, WA (US); Avi Van Haren, Vancouver (CA); Hugh Leung, Burnaby (CA); Yongkook Kim, Port Moody (CA); Ryan Neimy, North Vancouver (CA); Sergey Ovcharenko, Delta (CA)

(73) Assignee: Verathon Inc., Bothell, WA (US)

( * ) Notice: Subject to any disclaimer, the term of this patent is extended or adjusted under 35 U.S.C. 154(b) by 584 days.

(21) Appl. No.: 18/056,514

(22) Filed: Nov. 17, 2022

(65) Prior Publication Data

US 2023/0148850 A1     May 18, 2023

Related U.S. Application Data

(60) Provisional application No. 63/280,746, filed on Nov. 18, 2021.

(51) Int. Cl.
| | |
|---|---|
| *A61B 1/267* | (2006.01) |
| *A61B 1/00* | (2006.01) |
| *A61B 1/05* | (2006.01) |
| *A61B 1/06* | (2006.01) |

(52) U.S. Cl.
CPC .......... *A61B 1/267* (2013.01); *A61B 1/00066* (2013.01); *A61B 1/00126* (2013.01); *A61B 1/00128* (2013.01); *A61B 1/00142* (2013.01); *A61B 1/05* (2013.01); *A61B 1/0676* (2013.01); *A61B 1/00119* (2013.01)

(58) Field of Classification Search
CPC . A61B 1/00066; A61B 1/267; A61B 1/00119; A61B 1/00128; A61B 1/05; A61B 1/00117; A61B 1/00126; A61B 1/00142; A61B 1/0676; A61B 1/00096; A61B 1/00135; A61B 1/00121
See application file for complete search history.

(56) References Cited

U.S. PATENT DOCUMENTS

| | | | |
|---|---|---|---|
| 5,800,344 | A | 9/1998 | Wood, Sr. et al. |
| 6,135,948 | A | 10/2000 | Lee |
| 6,354,993 | B1 | 3/2002 | Kaplan et al. |
| 8,529,442 | B2 | 9/2013 | Pacey et al. |
| 8,864,657 | B2 | 10/2014 | Tydlaska |
| 10,405,738 | B2 | 9/2019 | Zhou et al. |
| 2005/0192481 | A1 | 9/2005 | Berci et al. |

(Continued)

OTHER PUBLICATIONS

Extended European Search Report issued for European Patent Application No. 25182738.2 dated Oct. 30, 2025, 8 pages.

*Primary Examiner* — Michael J Carey
*Assistant Examiner* — Olivia Grace Starkey
(74) *Attorney, Agent, or Firm* — Duane Morris LLP

(57) ABSTRACT

An apparatus comprises a video baton for insertion into a plurality of laryngoscope blade covers having different sizes and geometries. The video baton comprises: a handle portion, a shuttle assembly slidingly positioned within the handle portion between an extended position and a retracted position, and a flexible coupling element having a proximal end and a distal end. The flexible coupling element is coupled to the shuttle assembly at the proximal end and an image capturing and lighting assembly positioned at the distal end of the flexible coupling element.

19 Claims, 12 Drawing Sheets

(56)          References Cited

U.S. PATENT DOCUMENTS

| | | | | |
|---|---|---|---|---|
| 2006/0276693 A1* | 12/2006 | Pacey | .................... | A61B 1/267 |
| | | | | 600/188 |
| 2010/0261967 A1 | 10/2010 | Pacey et al. | | |
| 2011/0178372 A1 | 7/2011 | Pacey et al. | | |
| 2013/0096457 A1* | 4/2013 | Qiu | ........................ | A61B 1/267 |
| | | | | 600/549 |
| 2016/0262603 A1* | 9/2016 | Molnar | .................. | A61B 1/233 |
| 2019/0133430 A1 | 5/2019 | Inglis et al. | | |
| 2020/0178786 A1* | 6/2020 | Sabetrasekh | ....... | A61B 1/00073 |
| 2023/0125143 A1* | 4/2023 | Schmitt | .................. | A61B 1/015 |
| | | | | 600/104 |

* cited by examiner

DYNAMICALLY RETRACTABLE CAMERA FOR VIDEO LARYNGOSCOPE

CROSS-REFERENCE TO RELATED APPLICATION

This application claims priority under 35 U.S.C. § 119, based on U.S. Provisional Patent Application No. 63/280,746 filed Nov. 18, 2021, titled "Dynamically Retractable Camera for Video Laryngoscope," the disclosure of which is hereby incorporated by reference.

BACKGROUND

This present disclosure relates to video medical devices and, more particular, to a video laryngoscope having an image capturing component for allowing accurate examination of a patient's upper airway.

Endotracheal intubation provides the current preferred method for control of the airway for mechanical ventilation. The process involves passing an endotracheal tube (ETT) through the mouth, past the tongue, and to and through the vocal cords and larynx to seal the airway. This protects the openness of the airway and protects the airway from aspiration of gastric contents, foreign substances, or secretions.

Traditional laryngoscopes rely on opening the upper airway to provide a direct line of sight from the medical practitioner's eye to the larynx. Subsequent developments in laryngoscopes utilized fiberoptic bundles, sometimes coupled to video displays. More recently, laryngoscopes with video cameras have made it possible to display the image of the airway anatomy from a remote position, and in some instances allow the medical technician to identify relevant anatomical landmarks without repositioning the patient. This technology reduces the past problem of difficult intubation when the glottis entrance cannot be adequately seen and further reduces the likelihood of infection by medical personnel being unduly close to the nose and mouth of the patient can be avoided.

DETAILED DESCRIPTION OF EMBODIMENTS

Figure 1A:
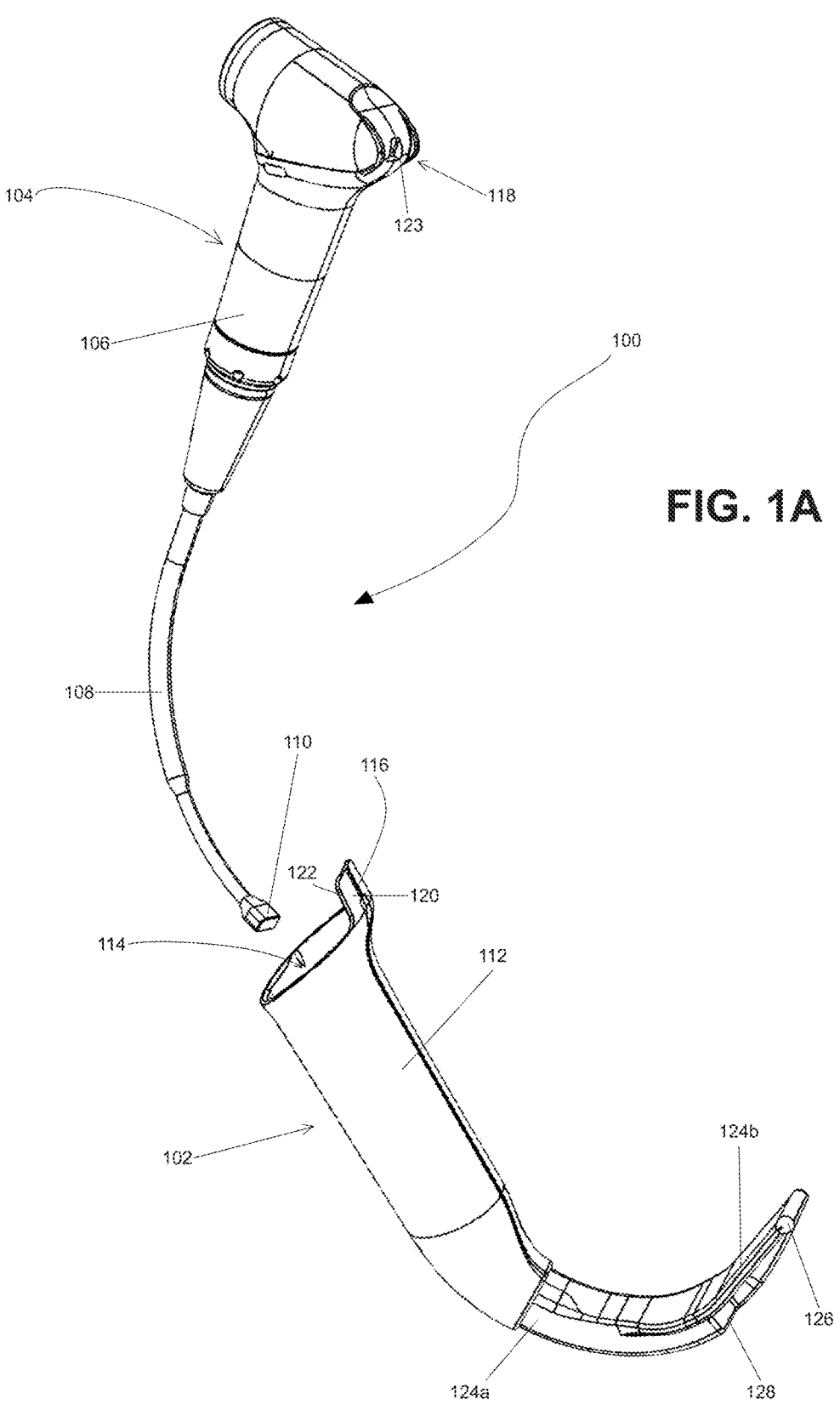
FIGS. 1A and 1B depict a substantially side and partially perspective view of a video laryngoscope having a blade cover configured to receive a detachable video baton therein, in uninstalled and installed configurations, respectively, consistent with embodiments described herein.

The following detailed description refers to the accompanying drawings. The same reference numbers in different drawings may identify the same or similar elements. Also, the following detailed description does not limit the invention.

Several embodiments of a video-based intubation laryngoscope and system are described that allow for examination of the upper airway during intubation. The system employs video laryngoscope embodiments configured to view a patient's glottis, reposition the patient's epiglottis, view the glottic aperture and convey video images of the patient's upper airway anatomy including the glottis and/or glottic aperture and surrounding area to a video monitor viewable by the laryngoscope user.

As described below, exemplary embodiments of the laryngoscope include a housing or blade cover intended for single use into which a reusable video baton is inserted. The video baton includes a video camera and a light source and is brought distally against an optical window located on the posterior side of the blade of the laryngoscope. Images obtained from the video baton are conveyed to a video monitor viewable by the laryngoscope user. The blade is used to reposition the epiglottis by engagement of the patient's vallecula, or alternatively, directly lifting the epiglottis to reveal the glottic aperture. An ETT loaded with a stylet is inserted into the mouth under direct vision and advanced until the tip of the ETT appears in the video monitor image, at or near the distal portion of the laryngoscope blade and proximal to the glottic aperture. Viewing the monitor, the ETT is then advanced forward through the glottic aperture into the patient's trachea, while the stylet is removed.

The laryngoscope blade cover, which is sometimes referred to as a "stat," includes a handle portion and a blade portion configured to engage the epiglottis to reveal the glottic aperture. As described herein, different sizes and geometries of laryngoscope blade covers may be provided for use with differently sized patients or patients having different anatomical geometry. Among other features, each laryngoscope blade cover includes an inner chamber that spans from the handle and terminates with an optically clear window on the posterior side of the blade directed toward the distal end. The inner chamber is configured to receive a video camera and lighting unit or video baton therein. As described herein, the video camera unit includes a video camera and a light source to illuminate an anatomical region within the field of view of the lens. The removable video camera and lighting unit is sufficiently sealed within the internal chamber to prevent moisture or fluids from reaching the internal optical electronics of the video camera and lighting member.

Consistent with implementations described herein, the video baton includes a dynamically retractable configuration that allows a single video baton to be used with a variety of differently sized and shaped laryngoscope blade covers. As described in detail below, in one implementation, an image capturing assembly is coupled to a sliding shuttle assembly that allows for the image capturing assembly to be freely moved longitudinally within the baton body. The movable components may be sealed with respect to the baton body to prevent ingress of contaminants and to all for reconditioning and sterilization of the video baton between uses.

Figure 1B:
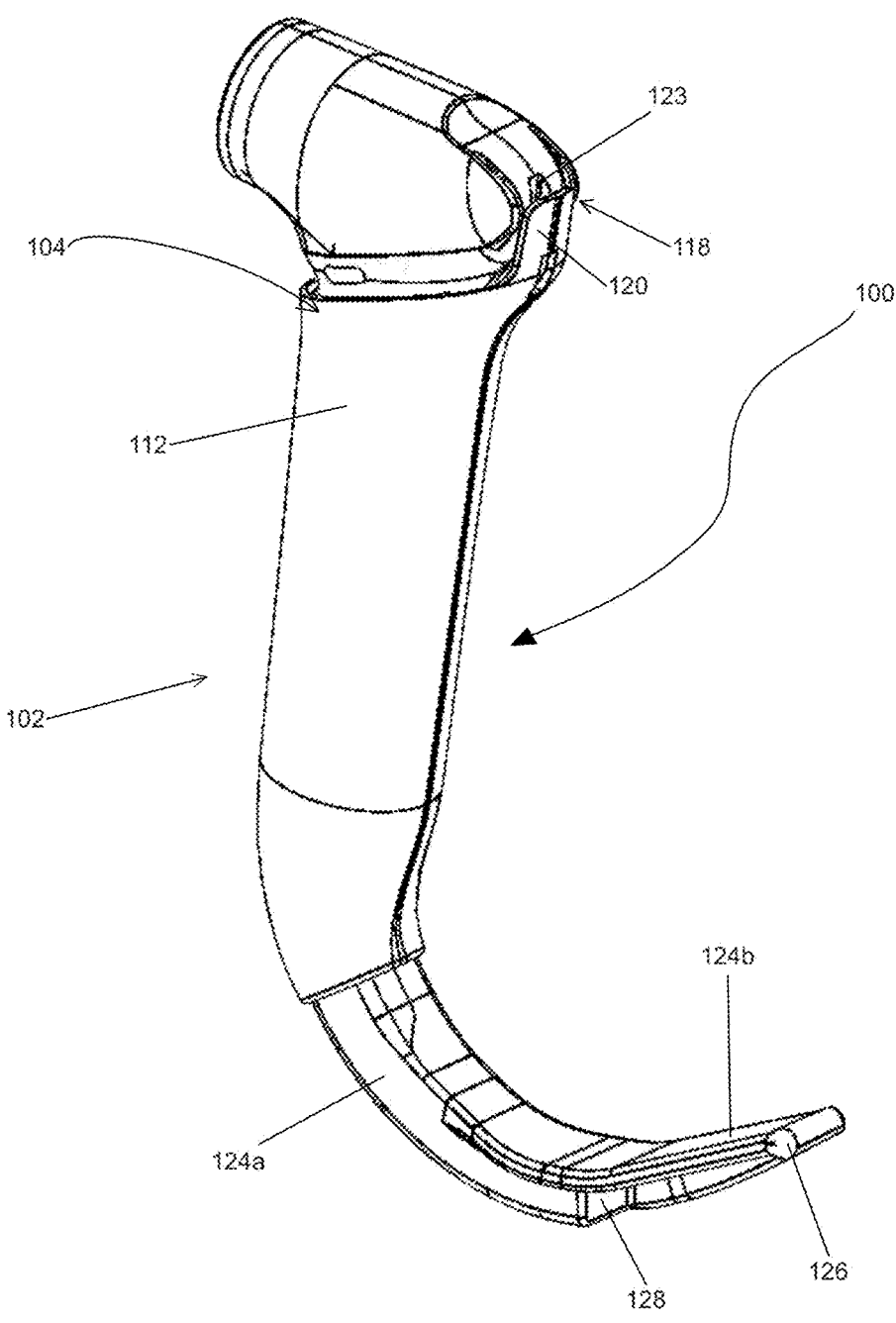

FIGS. 1A and 1B depicts a substantially side and partially perspective view of a video laryngoscope 100 having a blade cover 102 configured to receive a detachable video baton 104 therein in uninstalled and installed configurations, respectively. As shown, video baton 104 includes a substantially rigid handle portion 106, a flexible coupling element 108 extending from the handle portion 106, and an image capturing and lighting assembly 110 coupled to a distal end of flexible coupling element 108. In exemplary implementations, video baton 104 may be intended for multiple uses with individual single-use (i.e., disposable) or sterilizable blade covers 102, where each individual blade cover 102 is intended for single-use events in a patient. In some embodiments, blade cover 102 may be transparent or opaque and includes a blade cover handle 112 defining a chamber 114 similarly shaped to and slightly larger than the video baton 104.

As shown in FIGS. 1A and 1B, blade cover 102 may include a clip portion 116 that engages a corresponding clip portion 118 of video baton 104 to retain video baton 104 within blade cover 102 during use. For example, as shown in FIG. 1, blade cover 102 may be formed of a plastic or polymeric material. Clip portion 116 may include a projection 120 that extends upwardly from blade cover handle 112 and includes a tab portion 122 that extends inwardly therefrom. Corresponding clip portion 118 in video baton 104 includes a notch 123 that aligns with tab portion 122. During assembly, video baton 104 is seated within chamber 114 in blade cover 102 until tab portion 122 engages video baton 104. Continued urging of baton 104 within blade cover 102 causes projection 120 to deflect slightly to allow tab portion 122 to become seated within notch 120. When it is desired to remove video baton 104 from blade cover 102, projection 120 may be manually deflected (e.g., by a user's thumb) to allow tab portion 112 to escape notch 120, thereby allowing video baton 104 to be removed from blade cover 102. In other implementations, clip portion 116 of blade cover 102 and clip portion 118 video baton 104 may include different configurations, such as a reversed arrangement in which video baton 102 includes the tab portion and blade cover 102 includes the corresponding notch.

As further shown in FIG. 1, blade cover 102 includes a blade portion 124 that includes a proximal end 124a and a distal end 124b. Distal end 124b of blade portion 124 terminates with distal tip 126 for lifting the epiglottis or for engaging the vallecula of a patient to lift the epiglottis to reveal the glottic aperture. Distal end 124b further includes a window 128 positioned on the posterior side thereof. As described below, an image capturing assembly in video baton 104 is configured to engage window 128 when video baton 104 is fully inserted into blade cover 102, as shown in FIG. 1B. Consistent with implementations described herein, video baton 104 may be configured adjustable to accommodate insertion within different sized blade covers 102, while maintaining the image capturing assembly in operational abutment with window 128.

Figure 2A:
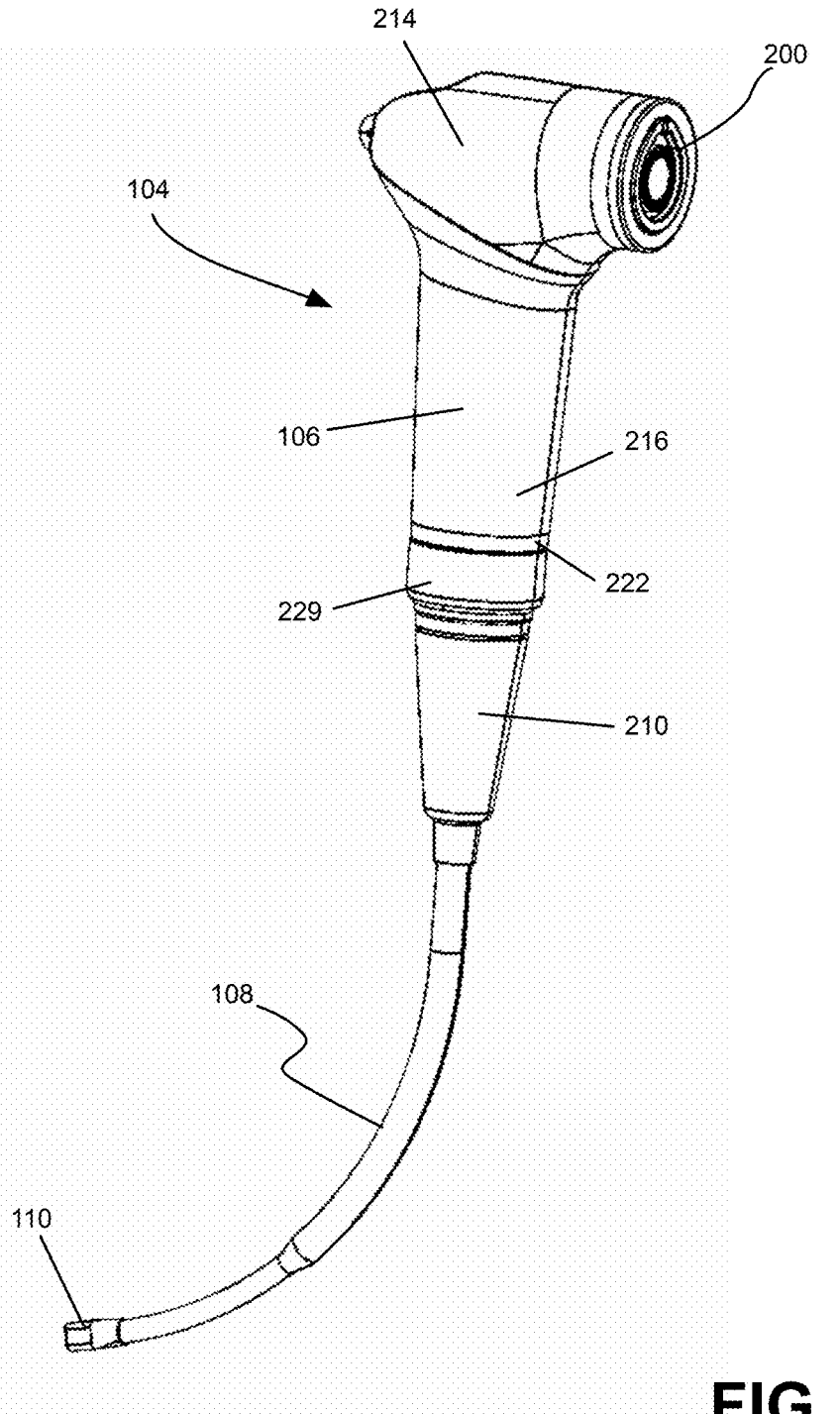
FIGS. 2A and 2B are isometric and exploded isometric views of a video baton consistent with an embodiment described herein.
Figure 2B:
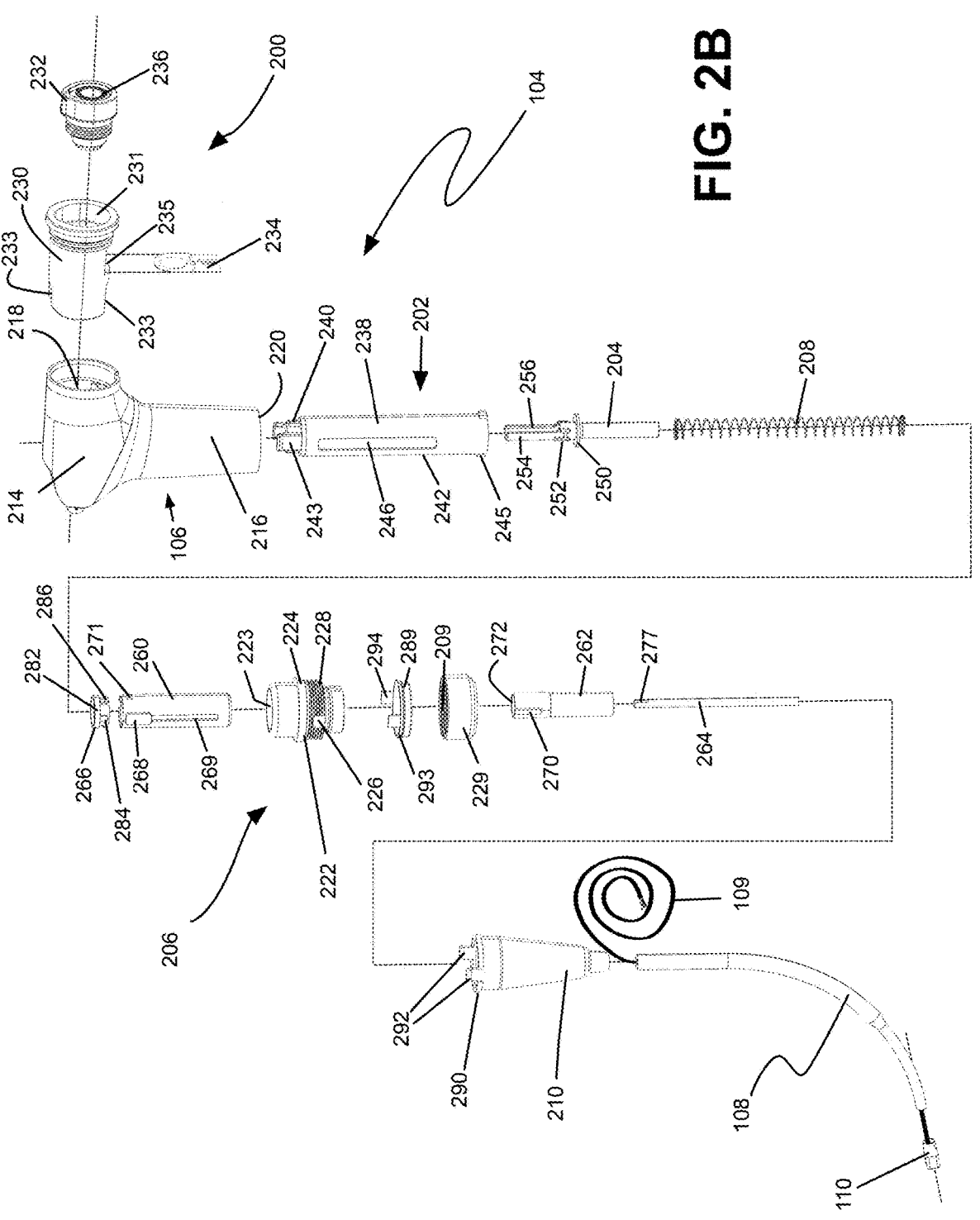
Figure 2C:
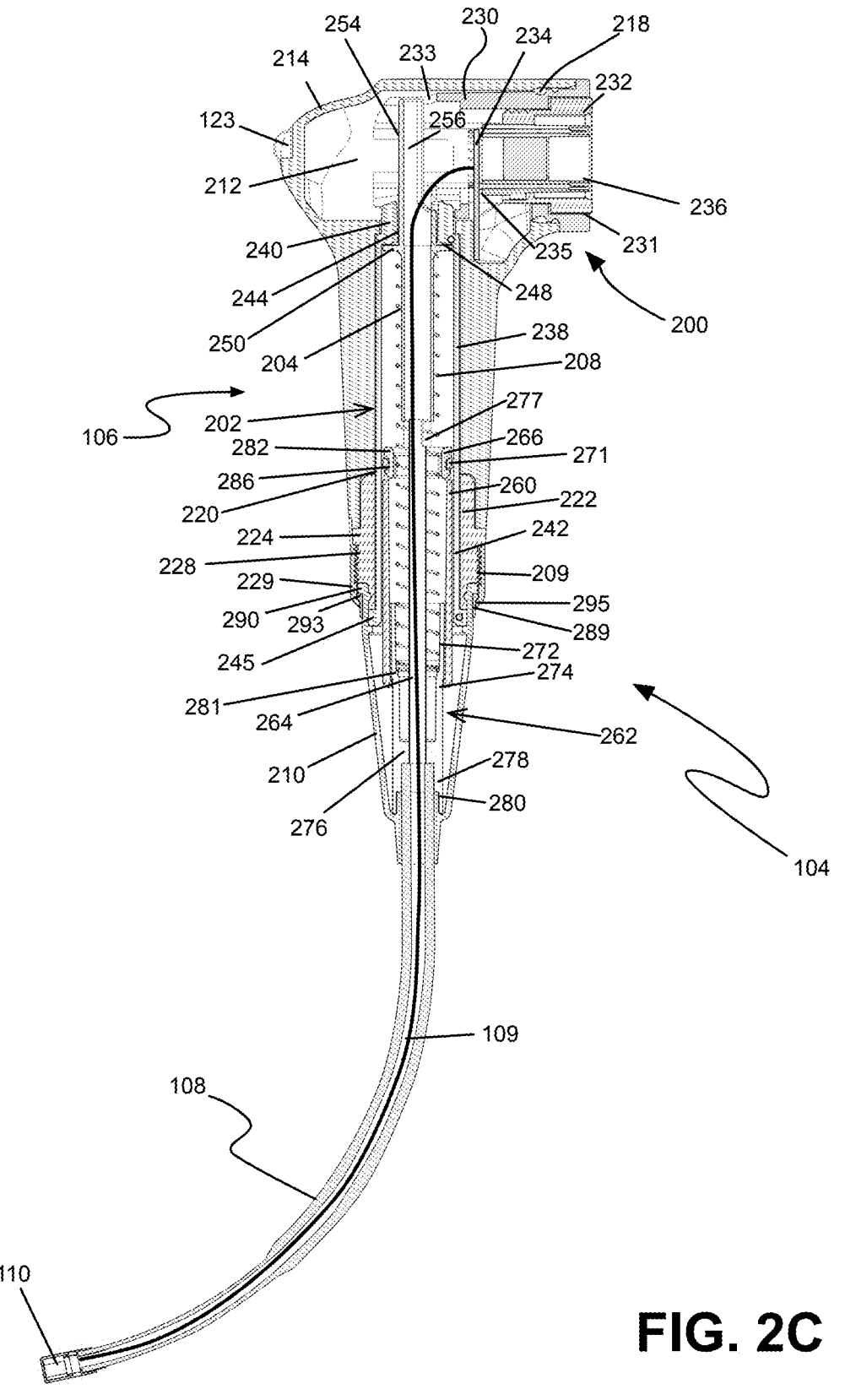
FIGS. 2C and 2D are side cross-sectional, and rear cross-sectional views, respectively of the video baton of FIGS. 2A and 2B, in an extended or uncompressed configuration.
Figure 2D:
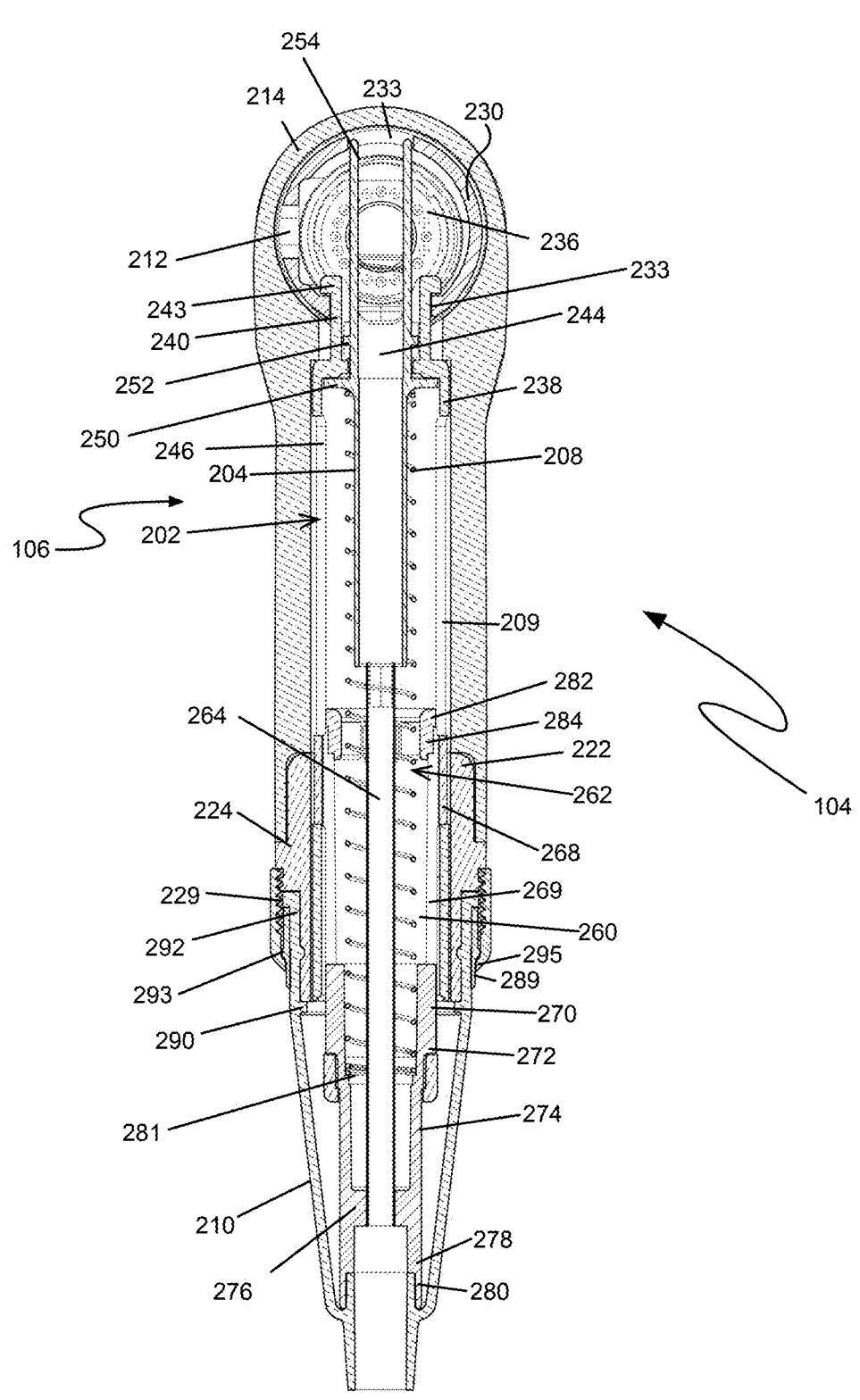
Figure 2E:
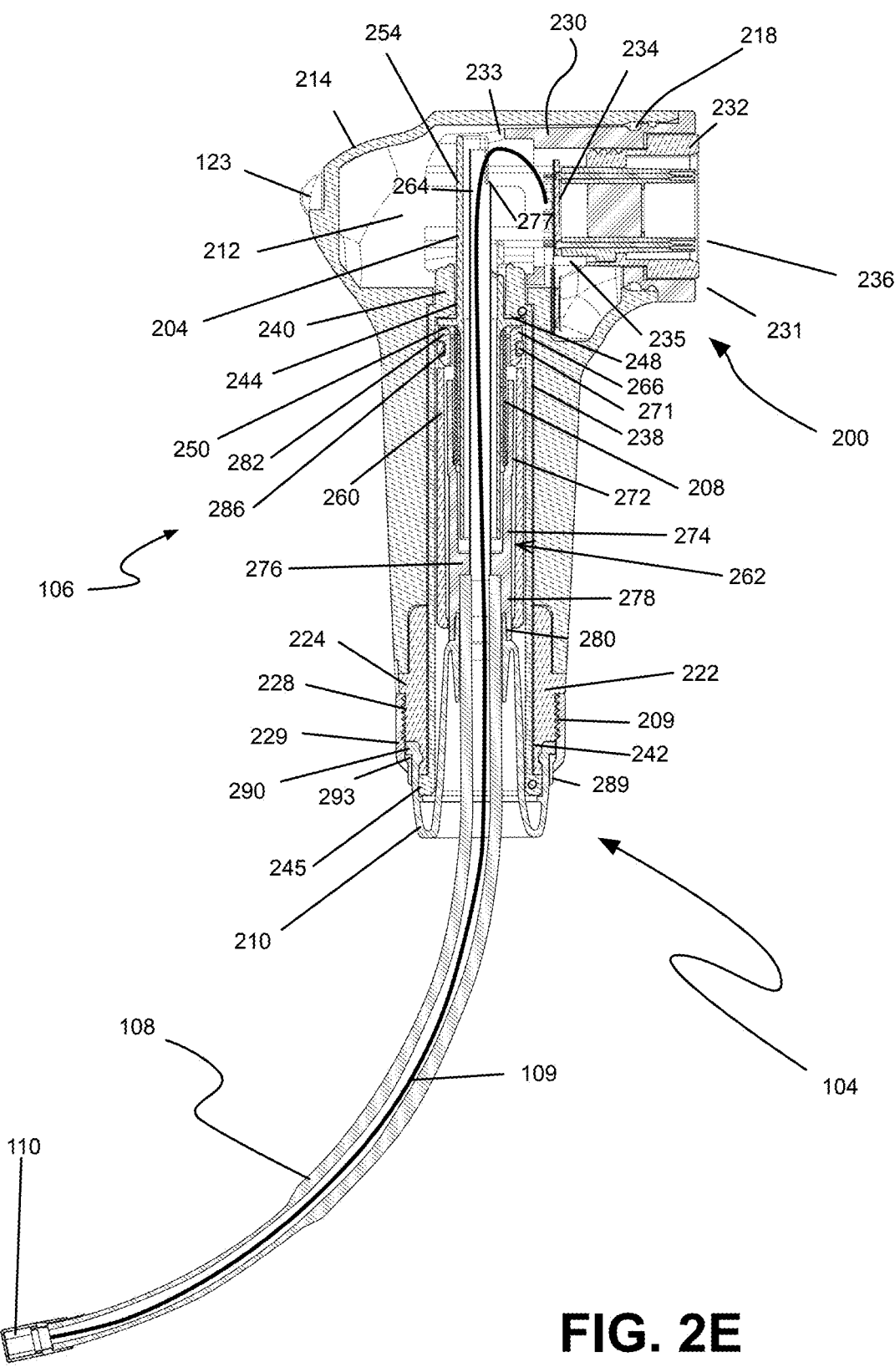
FIG. 2E is a side cross-sectional view the video baton of FIGS. 2A and 2B, in a retracted or compressed configuration.

FIGS. 2A and 2B are isometric and exploded isometric views of a video baton 104 consistent with a second embodiment described herein. FIGS. 2C and 2D are side cross-sectional, and rear cross-sectional views, respectively of video baton 104 in an extended or uncompressed configuration. FIG. 2E is a side cross-sectional view of video baton 104 in a retracted or compressed configuration. As briefly described above, video baton 104 is generally configured for reception within chamber 114 in blade cover 102, such that flexible coupling element 108 is received within blade portion 124 and handle portion 106 is received within handle 112 of blade cover 102. As shown in the FIGS. 2A-2E, consistent with one implementation described herein, video baton 104 includes handle portion 106, a receptacle assembly 200, a main rail 202, a cable guide tube 204, a shuttle assembly 206, a biasing element 208, a sealing element 210, flexible coupling element 108, and image capturing and lighting assembly 110.

As described above, handle portion 106 encloses most components of video baton 104 within an inner chamber 212 formed therein (as shown in FIG. 2C) and includes an upper portion 214 and a lower portion 216 that extends downwardly generally perpendicularly from upper portion 214. As shown in 2A, upper portion 214 includes an opening 218 that communicates with inner chamber 212 for receiving receptacle assembly 200. As described above, upper portion 214 of handle portion 106 includes clip portion 118 that engages corresponding clip portion 116 in blade cover 102.

Lower portion 216 of handle portion 106 includes an opening 220 for receiving main rail 202, shuttle assembly 206, and sealing element 210, as described in additional detail below. As shown in FIG. 2C, opening 220 also communicates with inner chamber 212. Consistent with implementations described herein, a generally tubular base portion 222 may be seated within opening 220 in lower portion 216 and secured thereto via, for example, an adhesive, such as an epoxy, ultrasonic welding, etc. Depending on chosen manufacturing method, base portion 222 and handle portion 216 could also be manufactured as a single piece. Base portion 222 may include a central opening 223, a flange 224 configured to engage an outer end of lower portion 216, a notched portion 226 for receiving a portion of the sealing element 210, and a threaded outer surface 228 for engaging an outer collar 229 to retain inner collar 289, which in turn retains sealing element 210 and main rail 202 in a coupled relationship with handle portion 106, as described in additional detail below.

Receptacle assembly 200 provides an interface between image capturing and lighting assembly 110 and an external video display (not shown). As shown in FIGS. 2A-2C, in one exemplary implementation receptacle assembly 200 includes a receptacle housing 230, a receptacle component 232, and a printed circuit board assembly (PCBA) 234. As shown in FIGS. 2B-2D, receptacle housing 230 is configured to be received within opening 218 in upper portion 214 of handle portion 106. Receptacle housing 230 includes a central opening 231 for receiving receptacle component 232 therein and a rear vertical slot 233 for engaging an upper portion of main rail 202 and for accommodating cable guide tube 204, as shown in FIG. 2D, and as described in additional detail below. In some implementations, receptacle housing 230 may further include a bottom slot 235 for receiving a portion of PCBA 234. Receptacle component 232 may include a connector interface element 236 for interfacing with a video cable (now shown) and PCBA 234. As shown in FIGS. 2A-2D, connector interface element 236 may include a multi-pin, magnetic configuration. In other implementations, different connector technologies may be used, such as high-definition multimedia interface (HDMI) or universal serial bus, type C (USB type C) connectors.

Although upper portion 214 and opening 218 are depicted in FIGS. 2A-2D as having a generally perpendicular configuration, in other implementations, opening 218, and receptacle assembly 200 received therein, may include alternative configurations, such as opening 218 extending approximately 135° relative to a longitudinal axis of upper portion 214.

PCBA 234 may include various imaging-related components to facilitate image capture by image capturing and lighting assembly 110 and transmission of captured imagery to an external display device via connector interface element

236. In some implementations, PCBA 234 may include wireless communications components (e.g., antenna(s), transceiver(s), etc.) for enabling wireless communication of images to a remote device.

Main rail 202 includes a generally tubular body 238 configured for reception within inner chamber 212 in lower portion 216 of handle portion 106. As shown in FIGS. 2B and 2D, main rail 202 includes an upper portion 240 configured to engage rear vertical slot 233 in receptacle housing 230 and a lower portion 242 configured to engage opening 223 in base portion 222. More particularly, upper portion 240 of main rail 202 may include a pair of flanges 243 about a central aperture 244. As shown in FIG. 2D, upper portion 240 and flanges 243 are sized to engage opposing sides of a lower portion of rear vertical slot 233 in receptacle housing 230, such that main rail 202 may be positively retained within inner chamber 212 upon assembly of receptacle housing 230 within handle portion 106. Lower portion 242 of main rail 202 may also include one or more flanges 245 for engaging an open end of base portion 222.

As shown in FIG. 2B, body 238 of main rail 202 further includes opposing longitudinal slots 246. As described below, longitudinal slots 246 are configured to receive corresponding projections in shuttle assembly 206 to prevent removal and rotation of shuttle assembly 206 relative to main rail 202. Main rail 202 includes an internal flanged portion 248 for engaging cable guide tube 204, as described below. Consistent with implementations described herein, main rail 202 may be formed as a two-part assembly (i.e., a split or halved assembly), such that cable guide tube 204 is longitudinally retained relative to main rail 202 upon assembly of video baton 104.

As shown in FIG. 2B-2E, cable guide tube 204 includes a generally tubular body configured to be received within body 238 of main rail 202. Cable guide tube 204 includes an external flanged portion and projection portions 252 for engaging flanged portion 248 of main rail 202, as shown in FIGS. 2C-2E. More specifically, a spacing between an upper surface of flanged portion 250 and a lower surface of projection portions 252 is substantially similar to a thickness of flanged portion 248 in main rail 202. Upon assembly of main rail 202 about cable guide tube 204, flanged portion 248 is captured between flanged portion 250 and projection portions 252 to lock cable guide tube 204 relative to main rail 202.

As shown in FIGS. 2B-2E, cable guide tube 204 includes an upper portion 254 that projects upwardly from flanged portion 248 and is configured to extend into upper portion 214 of handle portion 106 upon assembly. In some implementations, cable guide tube 204 may be secured relative to main rail 202 upon assembly. For example, cable guide tube 204 may be secured via a friction fit between flanged portion 248 of main rail 202 and flanged portion 250 of cable guide tube 204, an adhesive, etc. In other implementations, cable guide tube 204 is retained within handle portion 106 by virtue of outer collar 229 and biasing element 208. As shown in FIG. 2B, upper portion 254 of cable guide tube 204 includes a cutaway portion 256 that provides egress from cable guide tube 204 for wiring/cabling/flexible PCB 109, as shown in FIG. 2C. In other implementations, alternative mechanisms for supporting wiring/flexible PCB 109 as it egresses cable guide tube 204 may be employed. For example, a support element, such as a rod or bar may be incorporated within cavity 212 in upper portion 214 of handle portion 106 to provide a minimum bed radius over which PCB 109 passes.

Shuttle assembly 206 may include an arrangement of telescoping components configured to provide a retractable effective length to video baton 104. As shown in FIGS. 2B-2D, shuttle assembly 206 includes an upper shuttle component 260 concentrically receivable within main rail 202, a lower shuttle component 262 concentrically receivable within upper shuttle 260, a rigid tube element 264, and a cap element 266 for ensuring that lower shuttle component 262 is retained within upper shuttle component 260 following assembly.

Consistent with implementations described herein, upper shuttle component 260 includes a generally tubular configuration having a pair of opposing anti-rotation projections 268 for interfacing with longitudinal slots 246 in main rail 202 during assembly. Upper shuttle component 260 further includes a pair of opposing anti-rotation channels 269 for engaging corresponding projections 270 in lower shuttle component 262 and a pair of opposing notches 271 for engaging corresponding clip portions in cap element 266, as described below.

Lower shuttle component 262 also includes a generally tubular configuration sized for concentrically fitted reception within upper shuttle component 260. As shown in FIGS. 2B-2D, lower shuttle component 262 includes opposing anti-rotation projections 270 for engaging anti-rotation channels 269 in upper shuttle component 260. As shown in FIGS. 2B and 2C, lower shuttle component 262 includes a stepped inner configuration that includes a first portion 272 having a first inside diameter, a second portion 274 having a second inside diameter, a third portion 276 having a third inside diameter, a fourth portion 278 having a fourth inside diameter, and a fifth portion 280 having a fifth inside diameter.

As shown, first inside diameter of first portion 272 is configured to receive one end of biasing element 208 therein, such that biasing element 208 engages an interface shoulder 281 between first portion 272 and second portion 274. Second inside diameter of second portion 274 is smaller than the first inside diameter of first portion 272.

Third inside diameter of third portion 276 is smaller than the second inside diameter of second portion 274 and is sized to receive rigid tube element 264 therein. As shown in FIGS. 2B-2D, rigid tube element 264 includes a length substantially similar to shuttle assembly 206 and provides a clear pathway for wires/flexible PCB 109 or other components that extend from receptacle assembly 200 to image capturing and lighting assembly 110. In some implementations, an upper end of rigid tube element 264 may include a notched portion 277 for allowing wires/flexible PCB 109 to exit rigid tube element 264 when in a fully retracted configuration.

Fourth inside diameter of fourth portion 278 is larger than the third inside diameter of third portion 276 and is configured to engage an end of flexible coupling element 108 that extends outwardly from handle portion 106 for insertion within blade cover 102. Fifth inside diameter of fifth portion 280 is larger than the fourth inside diameter of fourth portion 278 and is configured to engage a portion of sealing element 210, as described below.

Cap element 266 includes a tubular configuration sized for fitted reception within upper shuttle component 260. As shown in FIGS. 2B-2D, cap element includes a flanged shoulder portion 282 having an outer diameter greater than an inside diameter of upper shuttle component 262, such that upon insertion of cap element 266 into upper shuttle component 260, shoulder portion 282 engages an upper surface of upper shuttle component 260 and prevents removal of lower shuttle component 262. As shown, cap element 266 further includes a pair of alignment projections 284 for engaging anti-rotation channels 268 in upper shuttle component 260. Cap element 266 also includes a pair of resilient clip portions 286 for engaging notches 271 in upper shuttle component 260. In one implementation, clip portions 286 may include a barbed configuration for securing cap element 266 to upper shuttle component 260 during assembly.

As shown in FIGS. 2B-2E, biasing element 208 is configured for concentric receipt within main rail 202, upper shuttle component 260, lower shuttle component 262, and cap element 266. In one implementation, biasing element 208 includes a helical spring configured to engage flanged portion 250 of main rail 202 on one end and interface shoulder 281 in lower shuttle component 262 on the other end. In this manner, following assembly, lower shuttle component 262 is biased away from handle portion 106 but may be urged toward handle portion 106 by compressing biasing element 208, thereby shortening an overall length of video baton 104 to fit within a shorter blade cover 102. Although a helical spring is described and illustrated herein, other alternative biasing mechanisms may be used, such as a resilient, compressible material, one or more flat springs, etc.

During assembly of video baton 104, rigid tube element 264 is seated within third portion 276 in lower shuttle component 262. Anti-rotation projections 270 in lower shuttle component 262 are then aligned with anti-rotation channels 269 in upper shuttle component 260 and lower shuttle component 262 is slid within upper shuttle component 260. Cap element 266 is then placed within upper shuttle component 260 and secured with clip portions 276 to form the assembled shuttle assembly 206.

Next, cable guide tube 204 is inserted within one half of main rail 202, as described above. Biasing element 208 is inserted longitudinally within shuttle assembly 206 such that rigid tube element 264 is concentrically positioned within shuttle assembly 206. Shuttle assembly 206 is then placed within the half of main rail 202, such that rigid tube element 265 is concentrically aligned with cable guide tube 204 and biasing element 208 is positioned concentrically over cable guide tube 204, as shown in FIGS. 2C and 2D. As briefly described above, anti-rotation projections 268 in upper shuttle component 260 are positioned within longitudinal slots 246 in the half of main rail 202. Subsequently, the second half of main rail 202 is aligned with the first half of main rail 202 and secured via, for example, an adhesive, such as an epoxy, ultrasonic welding, etc.

Assembled main rail 202 is then inserted within base portion 222 of handle portion 106 and receptacle assembly 200 is received and secured within opening 218 in upper portion 214 of handle portion 106.

Consistent with implementations described herein, sealing element 210 may include a cone formed of a resilient material, such as medical grade polyurethane, silicone rubber, or other flexible or rubber-like materials. As shown, sealing element 210 interfaces between lower portion 216 of handle portion 106 and fifth portion 280 of lower shuttle component 262, as shown in FIGS. 2C and 2D. Sealing element 210 functions to inhibit the ingress of debris or fluids into handle portion 106 that may cause adversely affect the operation of shuttle assembly 206. As lower shuttle component 262 is extended or retracted relative to handle portion 106, sealing element 210 may accommodate the changes without reducing seal function by either collapsing or extending the resilient cone.

As shown, sealing element 210, base portion 222 of handle portion 106, outer collar 229 and a second collar 289 together function to retain sealing element 210 in a non-rotatable relationship with handle portion 106. In particular, as shown in FIG. 2B, sealing element 210 includes a flanged portion 290, and a pair of opposing projections 292 having flanged upper surfaces and that project upwardly from flanged portion 290. Base portion 222 includes notched recesses 226 in threaded portion 228 for accommodating projections 292 during assembly, thereby preventing rotation of sealing element 210 relative to base portion 222 of handle portion 106. Second collar 289 includes a flanged portion 293 for engaging a lower surface of flanged portion 290 of sealing element 210 and further includes projections 294 for engaging the flanged upper surfaces of projections 292. As shown in FIGS. 2C and 2D, outer collar 229 includes a flanged lower portion 295 and a threaded portion 209. During assembly, rotation of outer collar 229 relative to base portion 222 urges flanged lower portion 295 into frictional engagement with a lower surface of flanged portion 293 in second collar 289, thereby securing sealing element 210 to handle portion 106.

As shown in FIG. 2E, when in a retracted configuration, first shuttle component 260 and second shuttle component 262 are urged upwardly relative to main rail 202 and against the biasing force of biasing element 208. To accommodate this position yet retain seal effectiveness, at least a portion of resilient sealing element 210 is inverted or collapsed within main rail 202. Such a retraction effectively reduces the length of video baton 104, thus allowing for insertion within different size blade covers 102. Although a fully retracted implementation is shown in FIG. 2E for exemplary purposes, it should be understood that shuttle assembly 206 may be positioned at any position within its range of travel, which is defined by the lengths of longitudinal slots 246 in main rail 202 and anti-rotation channels 269 in upper shuttle component 260.

During use, video baton 104 is inserted into chamber 114 in blade cover 102, which may be one of a variety of different sizes. Flexible coupling element 108 is inserted into blade portion 124 until image capturing and lighting assembly 110 engages window 128 in distal tip 124b of blade portion 124. Handle portion 106 is inserted into chamber 114 until clip portion 118 in handle portion 106 engages clip portion 116 in blade cover 102 to retain video baton 104 within blade cover 102. Depending on the size of blade cover 102, the urging of handle portion 106 within chamber 114 may cause biasing element 208 to compress to shorten the effective length of video baton 300, as described above, with smaller blade covers requiring more compression than larger blade covers. In this manner, a single re-usable video baton 104 may be used with a variety of differently sized blade covers 102

Figure 3A:
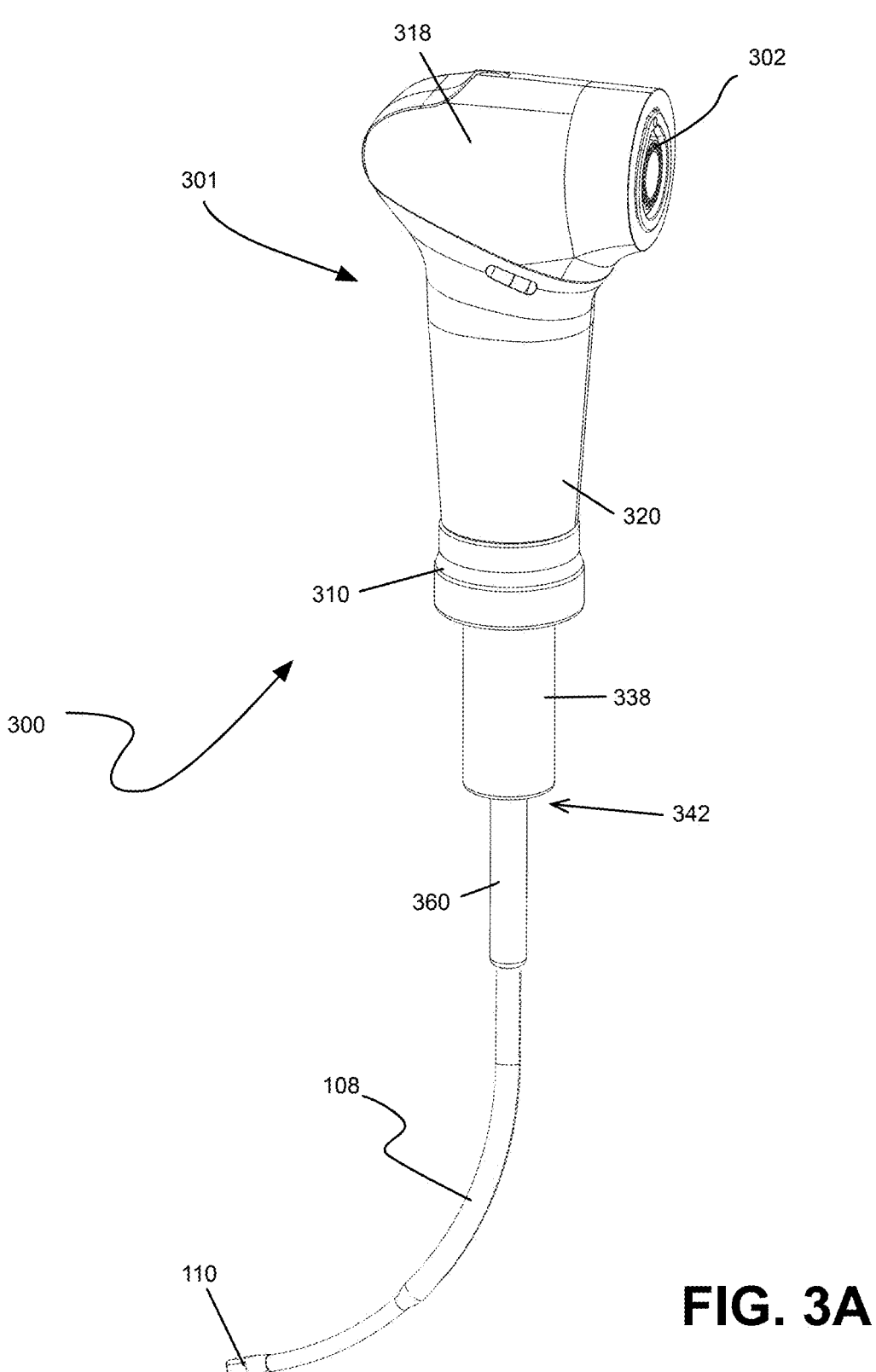
FIGS. 3A and 3B are isometric and exploded isometric views of a video baton consistent with a second embodiment described herein.
Figure 3B:
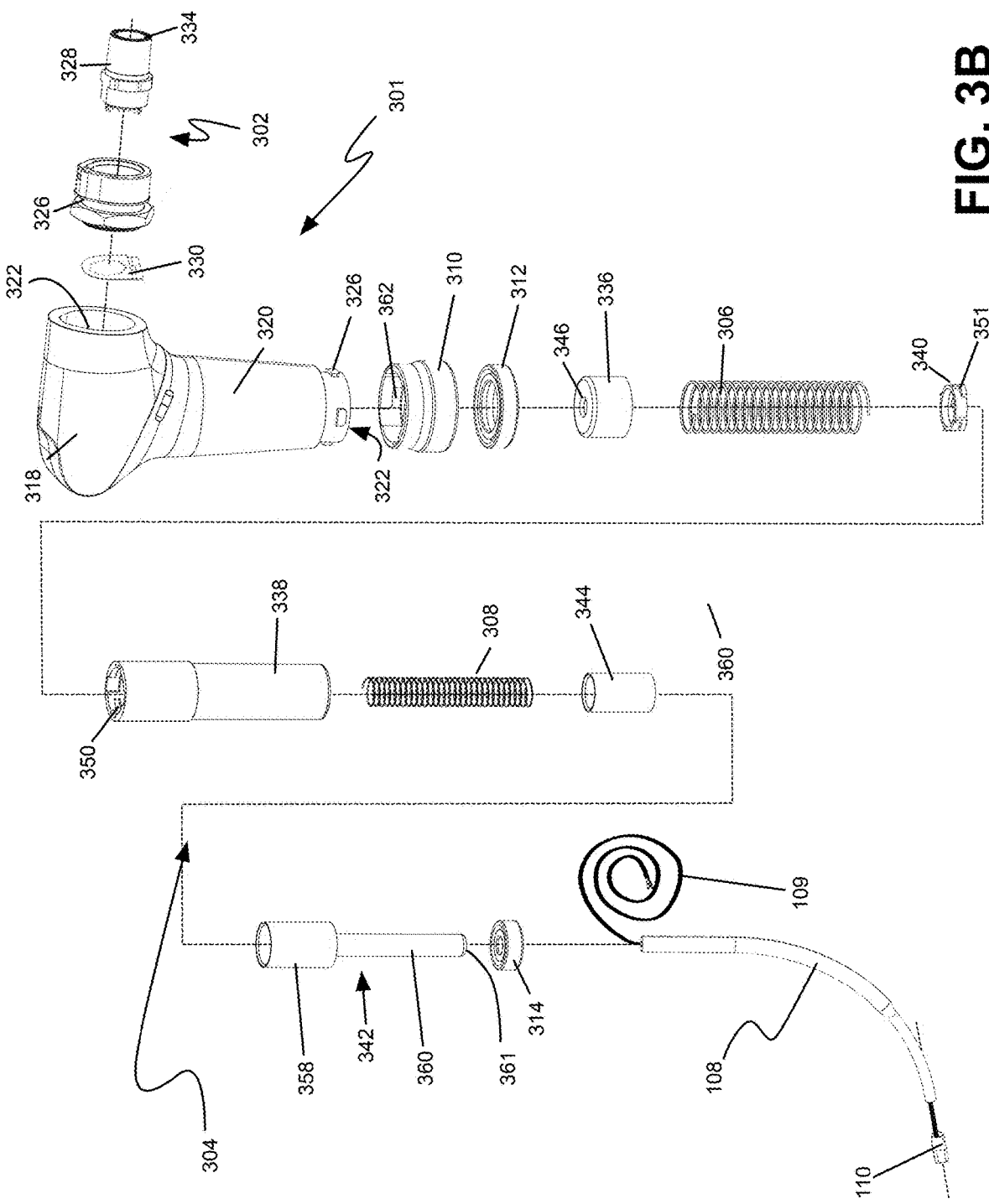
Figure 3C:
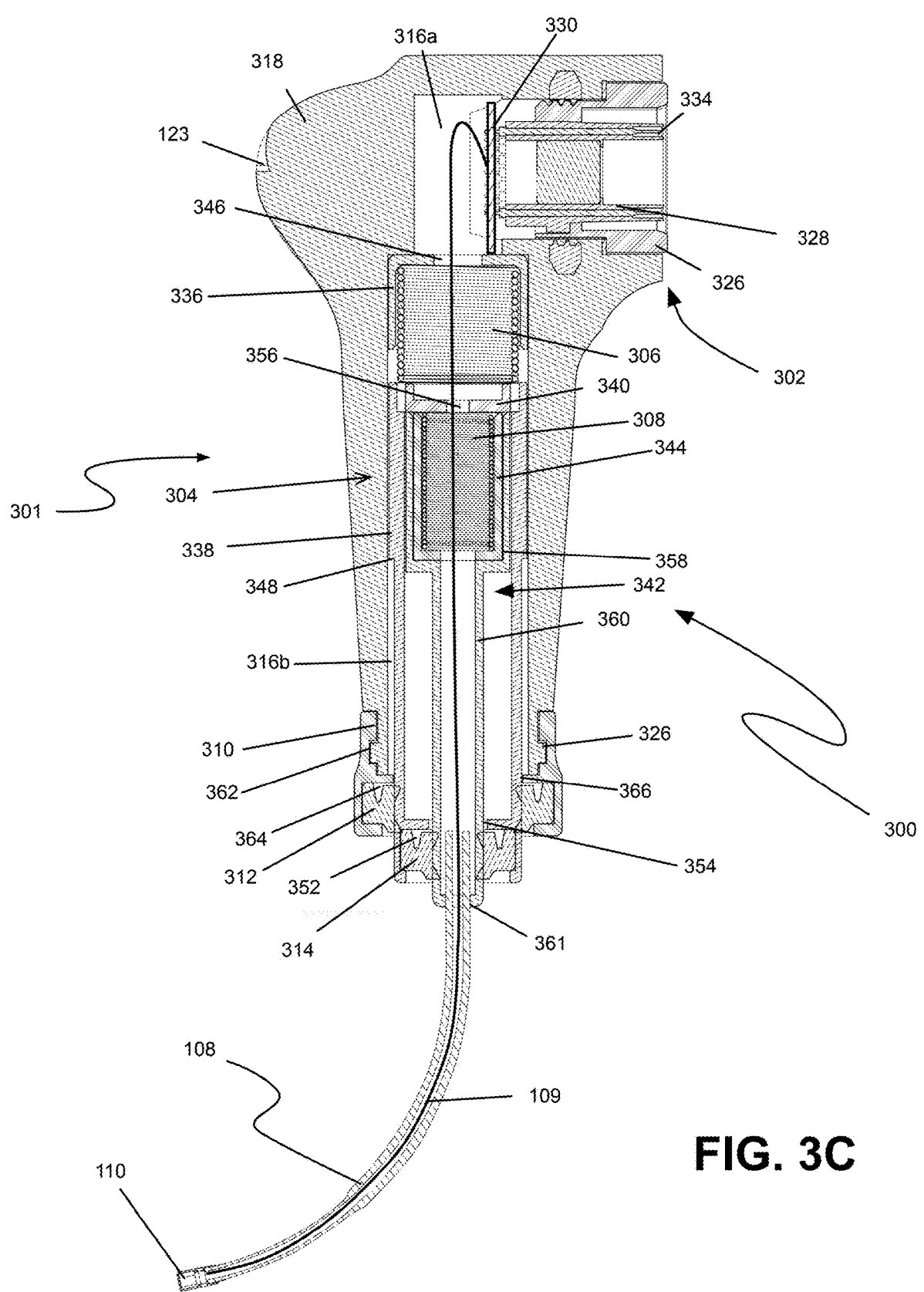
FIGS. 3C and 3D are side cross-sectional, and rear cross-sectional views, respectively of the video baton of FIGS. 3A and 3B, in a retracted or compressed configuration.
Figure 3D:
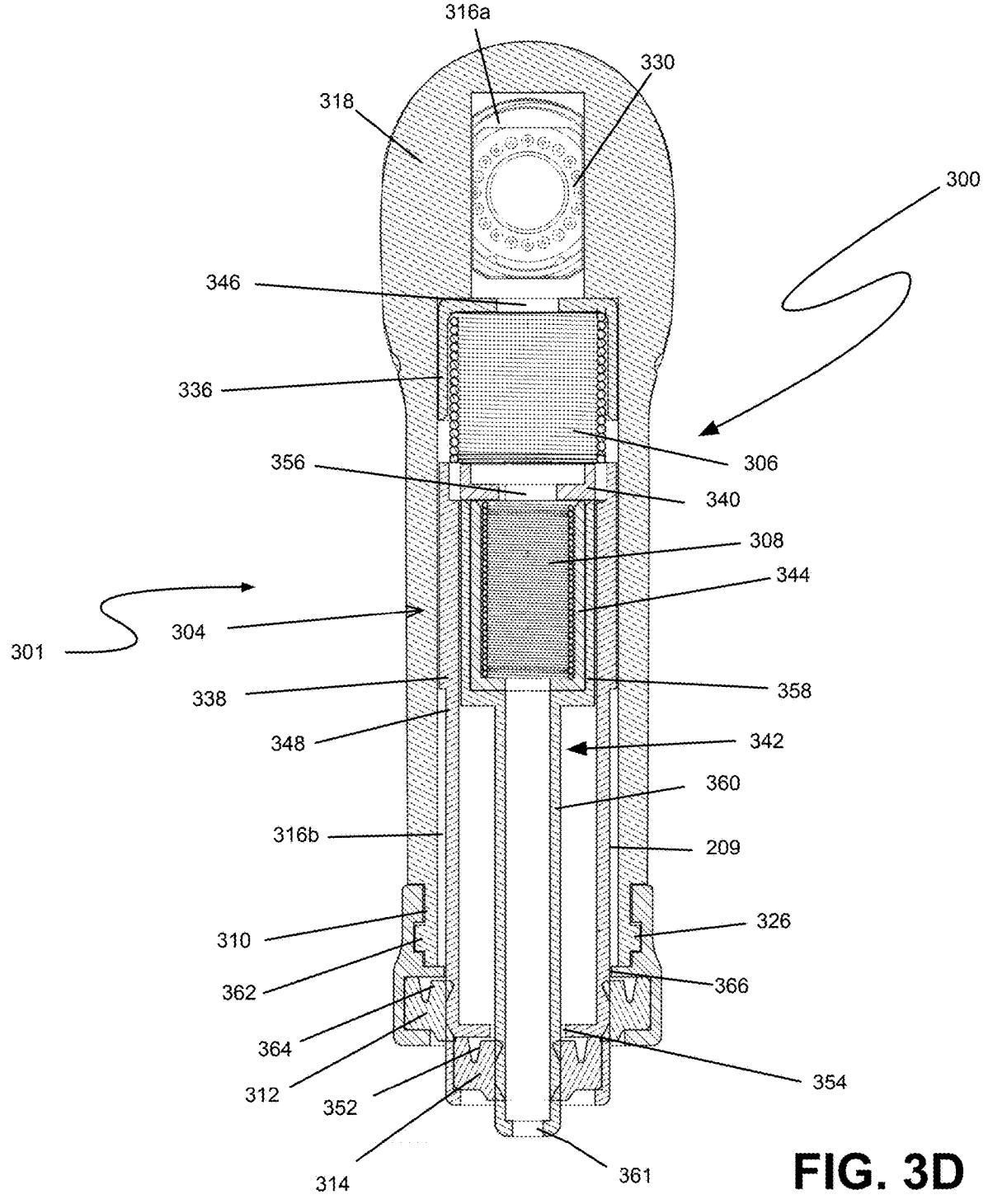
Figure 3E:
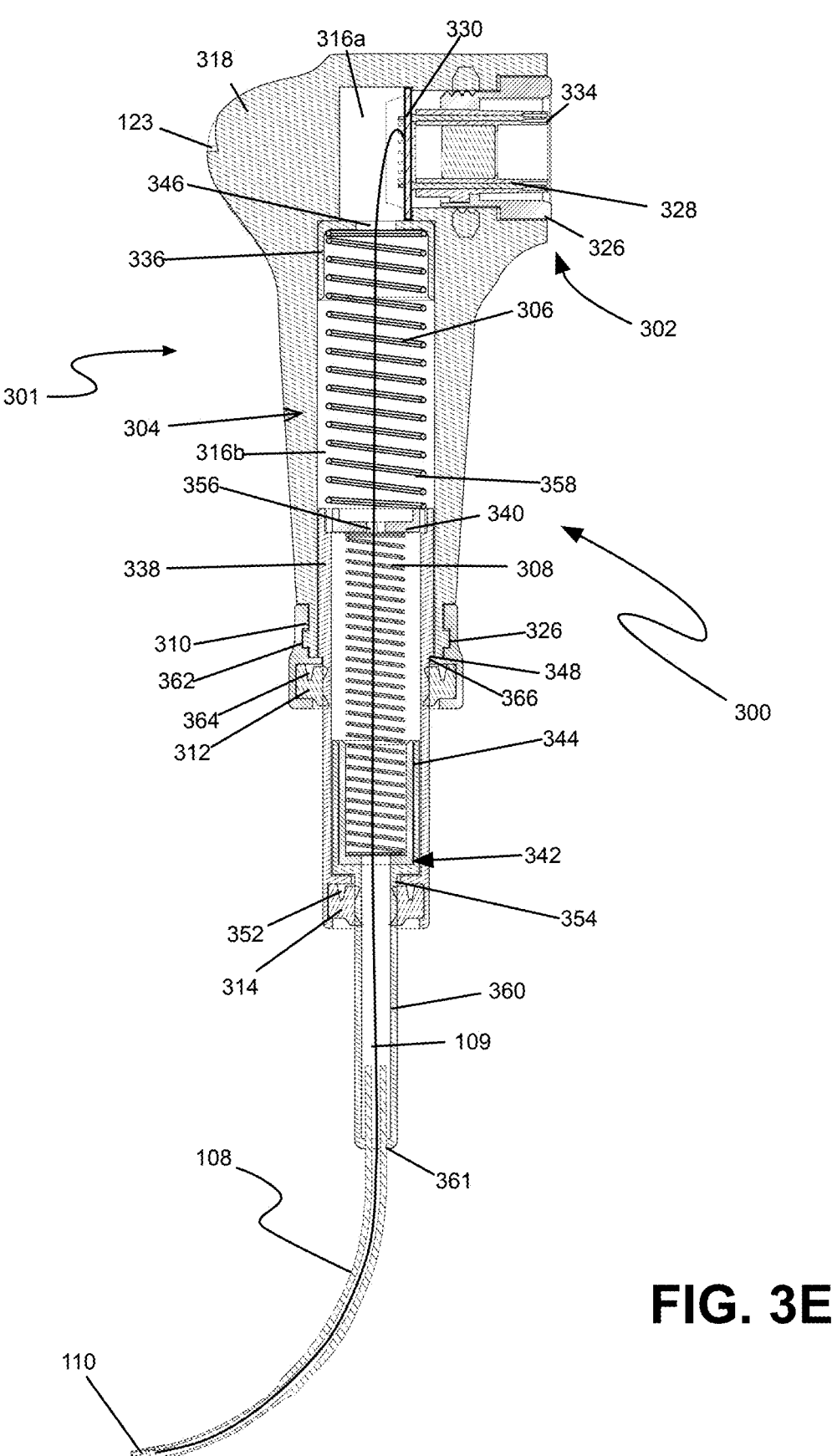
FIG. 3E is a side cross-sectional view the video baton of FIGS. 3A and 3B, in an extended or uncompressed configuration.

FIGS. 3A and 3B are isometric and exploded isometric views of a video baton 300 consistent with a second embodiment described herein. FIGS. 3C and 3D are side cross-sectional, and rear cross-sectional views, respectively of video baton 300 in a compressed or retracted configuration. FIG. 3E is a side cross-sectional view of video baton 300 in an uncompressed or extended configuration. As shown in the FIGS. 3A-3E, consistent with one implementation described herein, video baton 300 includes handle portion 301, a receptacle assembly 302, a shuttle assembly 304, first and second biasing elements 306 and 308, a collar element 310, first and second sealing elements 312 and 314, flexible coupling element 108, and image capturing and lighting assembly 110.

Similar to handle portion 106 described above, handle portion 301 encloses most components of video baton 104 within an inner chamber 316 formed therein (as shown in FIGS. 3C and 3D) and includes an upper portion 318 and a lower portion 320 that extends downwardly generally perpendicularly from upper portion 318. As shown in FIG. 3A, upper portion 318 includes an opening 322 that communicates with an upper portion 316a of inner chamber 316 for receiving receptacle assembly 302. Similar to handle portion 106 described above, upper portion 318 of handle portion 301 may also include clip portion 118 that engages corresponding clip portion 116 in blade cover 102.

Lower portion 320 of handle portion 301 includes an opening 324 for receiving shuttle assembly 304 therein, as described in additional detail below. As shown in FIGS. 3C and 3D, opening 324 communicates with a lower portion 316b of inner chamber 316. Lower portion 320 may further include one or more projections 326 for engaging corresponding portions in collar element 310 to secure collar element 310 to handle portion 106 during assembly, as described more fully below.

Receptacle assembly 302 provides an interface between image capturing and lighting assembly 110 and an external video display (not shown). As shown in FIGS. 3A-3C, in one exemplary implementation receptacle assembly 302 includes a receptacle housing 326, a receptacle component 328, and a printed circuit board assembly (PCBA) 330. As shown in FIGS. 3B-3E, receptacle housing 326 is configured to be received within opening 322 in upper portion 318 of handle portion 301. Receptacle housing 326 includes a central opening 332 for receiving receptacle component 328 therein. Receptacle component 328 may include a connector interface element 334 for interfacing with a video cable (now shown) and PCBA 330. As shown in FIGS. 3A-3D, connector interface element 334 may include a multi-pin, magnetic configuration. In other implementations, different connector technologies may be used, such as high-definition multimedia interface (HDMI) or universal serial bus, type C (USB type C) connectors.

PCBA 330 may include various imaging-related components to facilitate image capture by image capturing and lighting assembly 110 and transmission of captured imagery to an external display device via connector interface element 334. In some implementations, PCBA 330 may include wireless communications components (e.g., antenna(s), transceiver(s), etc.) for enabling wireless communication of images to a remote device.

Shuttle assembly 304 may include an arrangement of telescoping components concentrically received within lower inner chamber portion 316b of lower handle portion 320 configured to provide a retractable effective length to video baton 300. As shown in FIGS. 3B-3E, shuttle assembly 304 includes an upper shuttle spacer 336, an upper shuttle component 338, an upper shuttle cap 340, a lower shuttle component 342 concentrically receivable within upper shuttle component 338, and a lower shuttle spacer 344.

Consistent with implementations described herein, upper shuttle spacer 336 includes a generally tubular element sized to be received within an upper portion of chamber 316b. An upper portion of upper shuttle spacer 336 is radially enclosed to define a central aperture 346 therethrough that permits a clear pathway for wires or other components that extend from receptacle assembly 302 to image capturing and lighting assembly 110. As shown, an inside diameter of upper shuttle spacer 336 is sized to receive first biasing element 306 therein, as described below.

Upper shuttle component 338 includes a generally tubular element sized for reception within upper portion of chamber 316b. An outer surface of upper shuttle component 338 is configured to provide an engagement shoulder 348 that defines an outer travel boundary for upper shuttle component 338 within chamber 316b and prevents removal of upper shuttle component 338 from handle portion 301 after assembly. As shown in FIG. 3B, in one implementation, upper inside surface 350 of upper shuttle component 338 includes a notched or keyed configuration for receiving and engaging upper shuttle cap 340 upon assembly of lower shuttle component 342 and lower shuttle spacer 344 within upper shuttle component 338.

As shown in FIGS. 3C and 3D, a lower portion of upper shuttle component 338 defines an annular chamber 352 for receiving second sealing element 314, as described below. In one implementation, annular chamber 352 includes an upper aperture 354 sized to allow a portion of lower shuttle component 342 to extend therethrough, as described below. As shown, annular chamber 352 further includes a flanged lower configuration sized to allow second sealing element 314 to be received and retained within annular chamber 352.

Upper shuttle cap 340 may include a tubular component having a central aperture 356 therethrough configured to accommodate the wires/flexible PCB 109 from image capturing and lighting assembly 110. As shown in FIG. 3B, an outer surface of upper shuttle cap 340 may include a correspondingly notched or grooved configuration 351 for interlockingly engaging upper inside surface 350 of upper shuttle component 338 to prevent undesirable removal of upper shuttle cap 340 from upper shuttle component 338 after assembly.

Lower shuttle component 342 includes a generally tubular configuration having an upper portion 358 and a lower portion 360. As shown in FIGS. 3B-3E, upper portion 358 includes an outside diameter sized for concentric reception within upper shuttle component 338 and lower portion 360 includes a shaft having a reduced outside diameter sized for reception within aperture 354 in annular chamber 352 of upper shuttle component 338. As shown, lower portion 360 includes a bottom aperture 361 sized to receive and frictionally engage flexible coupling element 108 during assembly. Relative lengths of upper portion 358 and lower portion 360 together define the relative travel distance of lower shuttle component 342 within upper shuttle component 338. Lower shuttle spacer 344 includes another generally tubular element sized for concentric receipt within upper portion 358 of lower shuttle component 342 and having an open end and a reduced diameter end. In one implementation, lower shuttle spacer 344 may allow for functional modifications during assembly. In one embodiment, when lower shuttle spacer 344 is inserted as shown, the reduced internal diameter of spacer 344 (relative to upper portion 358 of lower shuttle component 342 allows for a reduced diameter biasing element 308 (described below). However, in a second embodiment (not shown), if lower shuttle spacer 344 is inserted into lower shuttle component 342 with its reduced diameter end facing upward, spacer 344 allows for a reduced travel of biasing element 308, thereby increasing a force with which lower shuttle is biased into an extended or uncompressed state.

As shown in FIGS. 3C and 3D, first biasing element 306 is positioned between upper shuttle spacer 336 and upper shuttle component 338 and functions to bias upper shuttle component 338 downwardly within chamber 316b. Second biasing element 308 is positioned within lower shuttle spacer 344 and engages upper shuttle cap 340 upon assembly to bias lower shuttle component 342 downwardly within upper shuttle component 338. In this manner, following assembly, shuttle components 338 and 342 are biased away from handle portion 301 but may be urged toward handle portion 301 by compressing biasing elements 306/308, thereby shortening an overall length of video baton 300 to fit within a shorter blade cover 102. Although helical springs are described and illustrated herein, other alternative biasing mechanisms may be used, such as a resilient, compressible material, one or more flat springs, etc.

Collar element 310 comprises a generally tubular element configured to engage handle portion 301 to retain shuttle assembly 304 within chamber 316*b*. As shown in FIGS. 3B-3E, collar element 310 may include one or more keyed notches 362 on an upper inside surface thereof for engaging projections 326 in lower portion 320 of handle portion 301. Upon assembly, keyed notches 362 interact with projections 326 to secure collar element 310 to handle portion 301.

A lower portion of collar element 310 defines an annular chamber 364 for receiving first sealing element 312, as described below. In one implementation, annular chamber 364 includes an upper aperture 366 sized to engage engagement shoulder 348 in the outer surface of upper shuttle component 338 when upper shuttle component 338 is in an extended configuration, as shown in FIG. 3E. As shown, annular chamber 364 further includes a flanged lower configuration sized to allow first sealing element 312 to be received and retained therein.

Consistent with implementations described herein, first and second sealing elements 312/314 include resilient seals, such as wiper seal. As shown in FIGS. 3C-3D, wiper seals 312/314 are sized for receipt within respective annular chambers 364/352 and include internal annular V-shaped grooves to allow sealing elements 312/314 to deflect upwardly or downwardly upon movement of upper shuttle component 338 and lower shuttle component 342, respectively. Sealing elements 312/314 function to inhibit the ingress of debris or fluids into handle portion 301 or between upper and lower shuttle components 338/342 that may cause adversely affect the operation of shuttle assembly 304.

During assembly of video baton 300, sealing elements 312/314 are inserted into respective annular chambers 364/352. Lower shuttle spacer 344 is inserted into upper portion 358 of lower shuttle component 342 and second biasing element 308 is inserted into lower shuttle spacer 344. The combined lower shuttle assembly is then inserted into upper shuttle component 338 and retained therein by upper shuttle cap 340.

Flexible coupling element 108 and wires/flexible PCB 109 are inserted through bottom aperture 361 in lower shuttle component 342 and wires/flexible PCB 109 are threaded through upper shuttle component 342. Upper shuttle spacer 336 is inserted into chamber 316*b* and first biasing element 306 is placed within upper shuttle spacer 336. Upper shuttle component 338 is then inserted into chamber 316*b* with first biasing element 306 engaging upper shuttle spacer 336 and upper shuttle component 342/upper shuttle cap 340. Wires/flexible PCB 109 are threaded through upper shuttle cap 340 and into upper chamber 316*a* for connection to PCBA 330 during assembly of receptacle assembly 302 to handle portion 301.

During use, video baton 300 is inserted into chamber 114 in blade cover 102, which may be one of a variety of different sizes. Flexible coupling element 108 is inserted into blade portion 124 until image capturing and lighting assembly 110 engages window 128 in distal tip 124*b* of blade portion 124. Handle portion 301 is inserted into chamber 114 until clip portion 118 in handle portion 301 engages clip portion 116 in blade cover 102 to retain video baton 300 within blade cover 102. Depending on the size of blade cover 102, the urging of handle portion 301 within chamber 114 may cause biasing elements 306/308 to compress to shorten the effective length of video baton 300, with smaller blade covers requiring more compression than larger blade covers. In this manner, a single re-usable video baton 300 may be used with a variety of differently sized blade covers 102

The foregoing description of exemplary implementations provides illustration and description but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements. Similarly, relative terms, such as "upper/lower", "front/rear", and "forward/backward" are used to depict relative positioning with respect to described components and do not refer to absolute or gravity-based relative positions. Embodiments described herein may be implemented in any suitable orientation.

What is claimed is:

1. An apparatus comprising:
   a video baton for insertion into a plurality of laryngoscope blade covers having different sizes and geometries,
   wherein each of the plurality of laryngoscope blade covers comprises a blade portion having a distal end that includes a window formed therein,
   wherein the video baton comprises:
      a handle portion,
      a shuttle assembly slidingly positioned within the handle portion between an extended position and a retracted position;
      a flexible coupling element having a proximal end and a distal end,
      wherein the flexible coupling element is coupled to the shuttle assembly at the proximal end; and
      an image capturing and lighting assembly positioned at the distal end of the flexible coupling element, wherein the image capturing and lighting assembly is configured to engage the window in the distal end of the blade portion when the video baton is fully inserted into one of the plurality of laryngoscope blade covers, wherein movement of the shuttle assembly between the extended position and the retracted position enables the flexible coupling element to automatically accommodate insertion into differently sized laryngoscope blade covers.

2. The apparatus of claim 1, wherein the handle portion comprises a central chamber, and wherein the apparatus further comprises:

a tubular main rail received within the central chamber;

wherein the shuttle assembly further comprises:

an upper shuttle component; and a lower shuttle component coupled to the flexible coupling element, wherein the lower shuttle component is slidingly positioned within the upper shuttle component, and wherein the upper shuttle component is slidingly positioned within the tubular main rail.

3. The apparatus of claim 2, wherein the tubular main rail includes at least one longitudinal slot therein and wherein the upper shuttle component includes at least one projection for engaging the at least one longitudinal slot to prevent rotation of the upper shuttle component relative to the tubular main rail.

4. The apparatus of claim 3, wherein the upper shuttle component includes at least one longitudinal slot therein and wherein the lower shuttle component includes at least one projection for engaging the at least one longitudinal slot in the upper shuttle component to prevent rotation of the lower shuttle component relative to the upper shuttle component.

5. The apparatus of claim 2, further comprising:

an upper shuttle cap secured to an upper end of the upper shuttle component to prevent egress of the lower shuttle component from the upper end of the upper shuttle component.

6. The apparatus of claim 2, further comprising:

a biasing element positioned between the lower shuttle component and an upper portion of the tubular main rail, wherein the biasing element is configured to provide retraction or extension of the lower shuttle component relative to the tubular main rail.

7. The apparatus of claim 6, wherein the biasing element comprises a helical spring.

8. The apparatus of claim 2, further comprising:

a receptacle assembly for providing an interface to a video display;

wiring or a flexible printed circuit board (PCB) for coupling the image capturing and lighting assembly to the receptacle assembly, wherein the wiring or the flexible PCB has a length suitable to accommodate the extended position and the retracted position.

9. The apparatus of claim 8, further comprising:

a cable guide tube positioned within the handle portion concentrically within the tubular main rail, wherein the cable guide tube provides an extended guide for the wiring or the flexible PCB to inhibit kinking or damage to the wiring or the flexible PCB when the shuttle assembly is moved between the extended position and the retracted position.

10. The apparatus of claim 1, further comprising:

a sealing element secured to the handle portion and the shuttle assembly to prevent ingress of debris or fluid into the handle portion.

11. The apparatus of claim 1, wherein the sealing element comprises a flexible cone, wherein, when the shuttle assembly is in the extended position, the flexible cone is extended outwardly from the handle portion, and wherein, when the shuttle assembly is in the retracted position, the flexible cone is collapsed and inverted within the handle portion.

12. An apparatus comprising:

a video baton configured for insertion into one of a plurality of laryngoscope blade covers having different sizes and geometries, wherein each of the plurality of laryngoscope blade covers comprises a blade portion having a distal end that includes a window formed therein, wherein the video baton comprises:

a handle portion;

a flexible coupling element having a proximal end flexibly secured to a distal end of the handle portion, wherein the flexible coupling element is configured to move between an extended configuration and a retracted configuration relative to the handle portion to accommodate insertion into differently sized laryngoscope blade covers;

an image capturing and lighting assembly positioned at a distal end of the flexible coupling element, wherein the image capturing and lighting assembly is configured to engage the window in the distal end of the blade portion when the video baton is fully inserted into one of the plurality of laryngoscope blade covers;

a receptacle assembly for providing an interface to a video display; and wiring or a flexible printed circuit board (PCB) for coupling the image capturing and lighting assembly to the receptacle assembly, wherein the wiring or the flexible PCB has a length suitable to accommodate the extended configuration and the retracted configuration, wherein movement of the flexible coupling element between the extended configuration and the retracted configuration enables the flexible coupling element to automatically accommodate insertion into differently sized laryngoscope blade covers.

13. The apparatus of claim 12, further comprising:

a cable guide tube positioned within the handle portion, wherein the cable guide tube provides an extended guide for supporting the wiring or the flexible PCB to inhibit kinking or damage to the wiring or the flexible PCB when the flexible coupling element is moved between the extended configuration and the retracted configuration.

14. The apparatus of claim 12, further comprising:

a sealing element having a proximal end secured to the distal end of the handle portion and the distal end secured to the flexible coupling element, wherein the sealing element is configured to prevent ingress of debris or fluid into the handle portion.

15. The apparatus of claim 14, wherein the sealing element comprises a flexible cone.

16. The apparatus of claim 15, wherein, in the extended configuration, the flexible cone is extended outwardly from the handle portion, and wherein, in the retracted configuration, the flexible cone is collapsed and inverted within the handle portion.

17. The apparatus of claim 15, wherein the flexible cone is formed of one of: a medical grade polyurethane or a silicone rubber.

18. The apparatus of claim 14, wherein the video baton further comprises:

a collar assembly for securing the proximal end of the sealing element to the distal end of the handle portion.

19. The apparatus of claim 18, wherein the collar assembly comprises:

an outer collar secured to the distal end of the handle portion, wherein the outer collar has a tubular configuration having a radially inwardly flanged portion at its distal end; and a second collar having a tubular configuration and having a radially outwardly flanged portion at its proximal end, wherein the sealing element comprises a radially outwardly flanged portion at its proximal end, wherein the radially outwardly flanged portion of the sealing element is secured to the distal end of the handle portion by compressing engagement with the second collar, and wherein the radially outwardly flanged portion of the second collar is secured to the proximal end of the sealing element and the distal end of the outer collar by compressing engagement with the radially inwardly flanged portion of the outer collar.

\*    \*    \*    \*    \*